US007939561B2

(12) United States Patent
Schellenger et al.

(10) Patent No.: US 7,939,561 B2
(45) Date of Patent: *May 10, 2011

(54) BLISTER PACKAGING FOR ACUTE PAIN REGIMENS

(75) Inventors: Norman D. Schellenger, Midlothian, VA (US); William R. Maichle, Lowell, NC (US); Carl L. Whatley, Jr., Montgomery, AL (US); Giorgio Reiner, Como (IT); Alberto Reiner, Como (IT)

(73) Assignee: APR Applied Pharma Research s.a., Balerna (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/348,634

(22) Filed: Feb. 7, 2006

(65) Prior Publication Data

US 2007/0184106 A1    Aug. 9, 2007

(51) Int. Cl.
*A61K 31/185* (2006.01)
*A61K 31/19* (2006.01)
(52) U.S. Cl. .................. 514/553; 514/557; 514/576
(58) Field of Classification Search .................. 514/553, 514/557, 576; 560/47
See application file for complete search history.

(56) References Cited

U.S. PATENT DOCUMENTS

| 3,558,690 | A |  | 1/1971 | Sallmann et al. |
| 4,689,218 | A |  | 8/1987 | Gazzaniga et al. |
| 5,458,879 | A | * | 10/1995 | Singh et al. .................. 424/400 |
| 6,974,595 | B1 |  | 12/2005 | Reiner et al. |
| 7,687,542 | B2 | * | 3/2010 | Reiner et al. .................. 514/553 |
| 7,700,125 | B2 | * | 4/2010 | Reiner et al. .................. 424/412 |
| 2005/0147671 | A1 |  | 7/2005 | Reiner et al. |
| 2005/0214363 | A1 |  | 9/2005 | Reiner et al. |
| 2005/0215643 | A1 |  | 9/2005 | Reiner et al. |
| 2006/0013896 | A1 |  | 1/2006 | Reiner et al. |

FOREIGN PATENT DOCUMENTS

| CA | 2131515 | 9/1994 |
| EP | 0 418 043 B1 | 12/1990 |
| EP | 0 466 640 A2 | 1/1992 |
| GB | A-2 401 547 | 11/2004 |
| WO | WO 94/03160 A | 2/1994 |
| WO | WO 96/14839 A | 5/1996 |
| WO | 97/44023 | 5/1997 |

OTHER PUBLICATIONS

Gennaro et al. (eds.), Remington's Pharmaceutical Science, 18th Edition, Mack Publishing Co., Easton, PA, 1990, only p. 1637 supplied.*
Gennaro et al. (eds.), Remington's Pharmaceutical Science, 18th Edition, Mack Publishing Co., Easton, PA, 1990, Chapters 75-92.*
Brizuela et al., "Drug Information," Chapter 7 in Remington's Pharmaceutical Science, 18th Edition, Mack Publishing Co., Gennaro et al. (eds.), Easton, PA, 1990, only pp. 49-59 supplied.*

McNeely W et al: "Ficlofenac-potassium in migraine: a review." Drugs Jun. 1999, vol. 57, No. 6, Jun. 1999, pp. 991-1003, XP009077504.
Database Internet [Online] Feb. 2005, Novartis Pharma: "Voltaren Dispers" XP002434112 retrieved from Internet accession No. http://www.fachinfo.de/pdf/00/59/005941.pdf.
Henry, D., et al; "Variability in risk of gastrointestinal complications with individual non-steroidal anti-inflammatory drugs; results of a collaborative meta-analysis"; BMJ; vol. 312, pp. 1563-1566, (1996).
Walker A.M.; "Quantitative studies of the risk of serious hepatic injury in persons using nonsteroidal antiinflammatory dugs"; Arthritis and Rheumatism. vol. 40, No. 2, pp. 201-108 (1997).
Gutthann, S.P., et al; "Nonsteroidal anti-inflammatory drugs and the risk of hospitalization for acute renal failure"; Arch. Intern. Med., vol. 156, pp. 2433-2439, (1996).
Amidon, G.L., et al; "A theoretical basis for a biopharmaceutic drug classification: The correlation of in vitro drug product dissolution and in vivi bioavailability"; Pharm. Research, vol. 12, No. 3, pp. 413-420, (1995).
U.S. Appl. No. 11/132,023, filed May 18, 2005, Reiner, et al.
U.S. Appl. No. 11/132,024, filed May 18, 2005, Reiner, et al.
U.S. Appl. No. 11/180,996, filed Jul. 13, 2005, Reiner, et al.
U.S. Appl. No. 11/030,537, filed Jan. 5, 2005, Reiner, et al.
U.S. Appl. No. 11/351,611, filed Feb. 10, 2006, Reiner, et al.
U.S. Appl. No. 11/455,120, filed Jun. 16, 2006, Reiner, et al.
U.S. Appl. No. 11/349,008, filed Feb. 7, 2006, Reiner, et al.
Neuvonen, P.J., "The effect of magnesium hydroxide on the oral absorption of ibuprofen, ketoprofen and diclofenac"; Br. J. Clin. Pharmac. vol. 31, pp. 263-266, (1991).
Neuvonen, P.J., et al; "Enhancement of drug absorption by antacids"; Clin. Pharmacokinet. 27 (2): pp. 120-128, (1994).
Neuvonen, P.J., et al; "Effect of magnesium hydroxide on the absorption of tolfenamic and mefenamic acids"; Eur. J. Clin. Pharmacol, 35: pp. 495-501, (1988).
Derendorf, H., et al; "Pharmacokinetics of diclofenac sodium after intramuscular administration in combination with triamcinolone acetate"; Eur. J. Clin. Pharmacol.., 31:363-365 (1986).
Terhaag, B., et al; "Bioavailability of a new effervescent tablet of diclofenac"; Int. J. Clin. Pharmacol. Ther., 38:546-551 (2000).
Lotsch, J. et al; "Popluation pharmacokinetics of fast release oral diclofenac in healthy volunteers: relation to pharmacodynamics in an experimental pain model"; Phamaceutical Research, vol. 17, No. 1, pp. 77-84, (2000).
Marzo, A., et al; "Pharmacokinetics of Diclofenac after oral administration of its potassium salt in sachet an tabled formulations"; Arzneim. Forsch., 50:43-47 (2000).
Reiner, V., et al; "Increased absorption rate of diclofenac from fast acting formulations containing its potassium salt"; Arzneim. Forsch., 51-885-890 (2001).
Fourtillan, J.B. et al; "Etude pharmacocinetique du piroxicam chez l'homme sain"; Therapie, vol. 38, pp. 163-170, (1983).
Brogden, R.N., et al; "Diclofenac sodium: A review of its pharmacological properties and therapeutic use in rheumatic diseases and pain of varying orgin"; Drugs, 20: pp. 24-48, (1980).

(Continued)

*Primary Examiner* — Lawrence E Crane
(74) *Attorney, Agent, or Firm* — Arnall Golden Gregory LLP; Clark G. Sullivan

(57) ABSTRACT

Provided are rapidly bioavailable solid oral dosage forms of acute pain medications, and moisture resistant packaging that enables the formulation of such rapidly bioavailable tablet dosage forms. Also provided is packaging that discourages the use of rapidly bioavailable acute pain medications for off-label chronic pain treatment, and that allows such dosage forms to be manufactured and stored for prolonged periods of time.

22 Claims, 6 Drawing Sheets

OTHER PUBLICATIONS

Macia, M.A., et al: "Comparative bioavailability of a dispersible formulation of diclofenac and finding of double plasma peaks"; Int. J. Clin Pharmacol. Ther., 33:333-339 (1995).

Bettini, R., et al; "Swelling force development as a result of hydrate formation in diclofenac sodium or nitrofurantoin tablets", S.T.P. Pharma Sciences 10 (4) pp. 335-339, (2000).

Henrikson, P.A., et al; Absorption and effect of diclofenac sodium after surgical removal of a lower wisdom tooth; Curr. Ther. Res., 31:30-36 (1982).

Degen, P.H., et al; "Pharmacokinetics of diclofenac and five metabolites after single doses in healthy volunteers and after repeated doses in patients"; Xenobiotica, 18:1449-1455 (1988).

Maggi, C.A., et al; "Comparative bioavailability of diclofenac hydroxyethylpyrrolidine vs diclofenac sodium in man"; Eur. J. Clin. Pharmacol., 38:207-208 (1990).

Mendes, G.B.B., et al; "Comparative bioavailability of two suspension formulations of potassium diclofenac in healthy male volunteers"; Int. J. Clin. Pharmacol. Thr., 32:131-135 (1994).

Crook, P.R., et al; "The pharmacokinetics of diclofenac sodium in patients with active rheumatoid disease"; Eur. J. Clin. Pharmacol., 21:331-334 (1982).

Willis. J.V., et al; "The pharmacokinetics of diclofenac sodium following intravenous and oral administration"; Eur. J. Clin. Pharmacol., 16:405-410 (1979).

Willis, J.V., et al; "The influence of food on the absorption of diclofenac after single and multiple oral doses"; Eur. J. Clin. Pharmacol., 19:33-37 (1981).

Reiss, W., et al; "Pharmacokinetics and metabolism of the anti-inflammatory agent Voltaren" Scand. J. Reumatol., Suppl. 22:17-29 (1978).

Physicians' Desk Reference; Novartis Pharmaceutical Corp., pp. 1830-1832 (2000).

Bakshi, R., et al; A double-blind, Placebo-controlled trial comparing the analgesic efficacy of two formulations of Diclofenac in postoperative dental pain; Current Therapeutic Research vol. 52, No. 3, pp. 435-442 Sep. 1992.

Dahlöf, C., et al; Diclofenac-K (50 and 100 mg) and placebo in the acute treatment of migraine; Cephalalagia 13, pp. 20-26 (1993).

McNeely, W., et al; Diclofenac-Potassium in Migraine: A Review; Drugs; 57; pp. 991-1003 (1999).

Mehlisch, D.R., et al; Single-dose therapy with Diclofenac potassium, aspirin, or placebo following dental impaction surgery, Today's Therapeutic Trends 12; (Suppl. 1) pp. 15-31 (1995).

The Diclofenac-K/Sumatriptan Migrain Study Group; Acute treatment of migraine attacks: efficacy and safety of a nonsteroidal anti-inflammatory drug, diclofenac-potassium, in comparison to oral sumatriptan and placebo; Cephalalgia 19, pp. 232-240 (1999).

Ridgway, D.; Analgesics for Acute Pain, Meeting the United States Food and Drug Administration's Requirements for Proof of Efficacy, Clin J. Pain vol. 20, No. 3, May/June pp. 123-132 (2004).

Diener, H-C, et al; Efficacy and tolerability of Diclofenac potassium sachets in migraine: a randomized, double-blind, cross-over study in comparison with Diclofenac potassium tablets and placebo; Blackwell Publishing Ltd. *Cephalalgia* 26, pp. 537-547 (2005).

Hofele, C.M., et al; Efficacy and tolerability of diclofenac potassium sachets in acute postoperative dental pain: a placebo-controlled, randomised, comparative study vs. diclofenac potassium tablets; 2006 Blackwell Publishing Ltd. Int. J Clin Pract, Mar. 2006, 60, 3, pp. 300-307.

Craig, C.R.; Opioid and Nonopioid Analgesics, Modern Pharmacology $4^{th}$ Edition, p. 437 (1994).

Adkin, D. A., et al; The effect of different concentrations of Mannitol in solution on small intestinal transit: Implications for drug absorption; Pharmaceutical Research, vol. 12, No. 3 (1995).

Adkin, D.A., et al; The effect of Mannitol on the oral bioavailability of Cimetidine; Journal of Pharmaceutical Sciences vol. 84, No. 12, Dec. 1995.

Kumar, A., et al.; The Mystery Ingredients: Sweeteners, Flavorings, Dyes and Preservatives in Analgesic/Antipyretic, Antihistamine/Decongestant, Cough and Cold, Antidiarrheal, and Liquid Theophylline Preparations; Pediatrics vol. 91 No. 5 May 1993.

Massiou. H., et al.; Effectiveness of oral Diclofenac in the acute treatment of common migraine attacks: a double-blind study versus placebo; Cephalalgia 11 (1991).

Del Bene, E., et al; Intramuscular Treatment of Migraine Attacks Using Diclofenac Sodium: A Crossover Clinical Trial; The Journal of International Medical Research; 15: 44-48 (1987).

* cited by examiner

MEAN PLASMA CONCENTRATION-TIME PROFILE OF DICLOFENAC MEASURED IN ALL VOLUNTEERS AFTER ORAL ADMINISTRATION OF $T_1$ FORMULATION. LINEAR SCALE. VERTICAL BARS ARE SD.

MEAN PLASMA CONCENTRATION-TIME PROFILE OF DICLOFENAC MEASURED IN ALL VOLUNTEERS AFTER ORAL ADMINISTRATION OF $T_2$ FORMULATION. LINEAR SCALE. VERTICAL BARS ARE SD.

MEAN PLASMA CONCENTRATION-TIME PROFILE OF DICLOFENAC MEASURED IN ALL VOLUNTEERS AFTER ORAL ADMINISTRATION OF R (VOLTARENE® RAPIDE) FORMULATION. LINEAR SCALE. VERTICAL BARS ARE SD.

BLISTER PACKAGING FOR ACUTE PAIN REGIMENS

FIELD OF THE INVENTION

The present invention concerns packaging that discourages the use of acute pain medications for off-label chronic pain treatment, and that allows such dosage forms to be manufactured and stored for prolonged periods of time. The invention particularly relates to acute pain medications that are characterized by rapid bioavailability.

BACKGROUND

Off-label use of medications is a major concern for the United States Food and Drug Administration, which approves drugs predominantly based on their intended use. When drugs are used "off-label," i.e. for indications not approved by the Food and Drug Administration, they are being used in treatments that have not undergone rigorous FDA review for safety and efficacy in the off-label indication. In recent years, FDA has become increasingly cognizant of the potential for such off-label uses, especially in acute pain medications which, while nominally approved for acute pain, have tremendous potential for abuse in the chronic pain market where long-term safety issues are paramount. To overcome its concerns, FDA has informally required applicants to study safety in such off-label uses before approving many drugs for their requested indications. These regulatory demands increase the cost of drug development tremendously, and discourage innovation for new drugs and clinical indications.

The bioavailability of pharmaceutical products is a critical concern in the design of acute pain medications. The pharmacokinetics of a drug, which measure the time it takes a drug to become bioavailable and its concentration profile in serum over time, can have a significant effect on the effectiveness of a drug, as well as its safety. Pharmacokinetics are of particular concern for drugs that require an immediate onset of action, such as drugs used in the treatment of acute pain.

Various factors can influence the time it takes for a drug to become bioavailable in therapeutically effective concentrations. For orally administered solid dosage forms, some of the most important parameters include the disintegration/dissolution time of the drug, the stability and solubility of the molecule in the gastrointestinal tract, and first pass metabolism, to mention just a few. For some drugs such as potassium diclofenac the pH of the formulation can also affect its bioavailability. For example, it is known that diclofenac potassium has a tendency to precipitate in an acidic environment, thereby making it less bioavailable. This problem is highlighted in bioavailability studies of Cataflam, a commercially marketed form of diclofenac potassium, which exhibits two concentration peaks in the bloodstream when orally ingested.

When rapid bioavailability is desired, preferred modes of administration include parenteral, inhalation, mucosal and buccal administration. Tablets and capsules are generally available only in immediate release, extended release, and delayed release formats, and are not typically employed when rapid bioavailability is desired because of the time it takes for the dosage form to dissolve, and the resulting delay in gastrointestinal absorption. A novel delivery system for orally delivering diclofenac in a rapidly bioavailable tablet has been proposed in PCT/EP97/02709 (published as WO 97/44023), but solid oral dosage forms based on this type of platform are clearly the exception and not the rule.

The use of blister packs to package pills has become increasingly popular among specialty dosage forms such as orally disintegrating tablets, and drugs that are administered according to a predetermined schedule, such a birth control pills. In addition, the inventors are aware of one diclofenac potassium tablet formulated for rapid bioavailability that is marketed in Europe and packaged in a conventional blister pack. Generally, a conventional blister card package provides a container for individual dosages of the medicament separately packaged for delivery of the individual dosage to a patient. Typically, a blister card package contains a number (usually about 6-8) of individual dosages on a card where each dosage is separately contained and can be separated by perforations such that it can be readily detached. The blister card package is usually constructed of several layers. The top layer is a container sheet or container formstock constructed of a rigid material having integrally formed cavities or wells designed to hold the dosage form. The container sheet is sealed to a closure sheet (or lidstock) generally constructed of a foil and paper laminate. The blister package can be designed for removal of the dosage form from the container in a variety of ways. In some packages, the dosage is removed by pressing it through the closure sheet, where the closure sheet is made from a rupturable material. In other designs, the closure sheet is designed to be peeled off from the container sheet to remove the dosage form. Alternatively, the blister is scored to form a weakened area enabling the user to tear the blister and expose the cavity containing the tablet.

OBJECTS OF THE INVENTION

It is an object of the invention to provide packaging that discourages the use of acute pain medications, especially solid oral dosage forms that are formulated to be rapidly bioavailable, for the treatment of chronic pain.

Another object of the invention is to provide packaging that facilitates acute pain dosing regimens.

Still another object of the present invention to increase the rate of bioavailability of orally ingested acute pain medications such as tablets and capsules.

Yet another object is to provide packaging for rapidly bioavailable solid oral dosage forms that preserves and enhances their bioavailability.

SUMMARY OF THE INVENTION

In one embodiment the invention provides a blister pack dosing regimen that (1) discourages the inappropriate use of acute pain medications for the treatment of chronic long-term pain, (2) provides convenient predictable dosing, and (3) enables the formulation of moisture sensitive and rapidly bioavailable dosage forms for treating acute pain. By packaging no more than fourteen days of medication in a blister pack, and dividing the blister pack into segments for each day, a drug manufacturer can meet the needs of acute pain sufferers who typically need no more than 14 days worth of medication, and at the same time discourage use of the medication by sufferers of chronic pain who require prescriptions that last at least thirty days.

Therefore, the invention provides a method of packaging an acute pain medication, preferably diclofenac potassium, to discourage its use in the treatment of chronic pain comprising: (a) formulating said drug in a rapidly bioavailable dosage form; and (b) packaging said drug in a blister package divided into from five to fourteen medication segments, wherein: (i) each medication segment corresponds to one day of treatment, and (ii) each medication segment is divided into from one to four unit doses corresponding to a daily dosage for said drug. Finally, the invention also provides a method of treating a patient suffering from acute pain using the thus packaged acute pain medications.

In addition, it has unexpectedly been discovered that diclofenac potassium tablets, particularly those formulated for rapid disintegration and dissolution, can be made to disintegrate and dissolve faster by limiting their moisture uptake during storage, and allowing them to become harder over time. Whereas one would normally expect a tablet to disintegrate faster as it softens, the inventors have discovered that diclofenac potassium tablets disintegrate slower when the tablet softens, and that the tablet will not become softer if it is protected from moisture. In other words, the inventors have discovered that one can make diclofenac potassium tablets disintegrate faster, and hence be more rapidly bioavailable, simply by preventing them from absorbing moisture during storage, by using an appropriately designed blister packaging system. These results are counterintuitive and support the patentability of the present invention. Therefore, in another embodiment the diclofenac packaging system of the present invention is developed to prevent the packaged tablets from absorbing more than 2.0 wt. % moisture in three months when stored at 40° C. and 75% relative humidity, and thereby enhancing their bioavailability.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE PREFERRED EMBODIMENTS

Definitions

Figure 1:
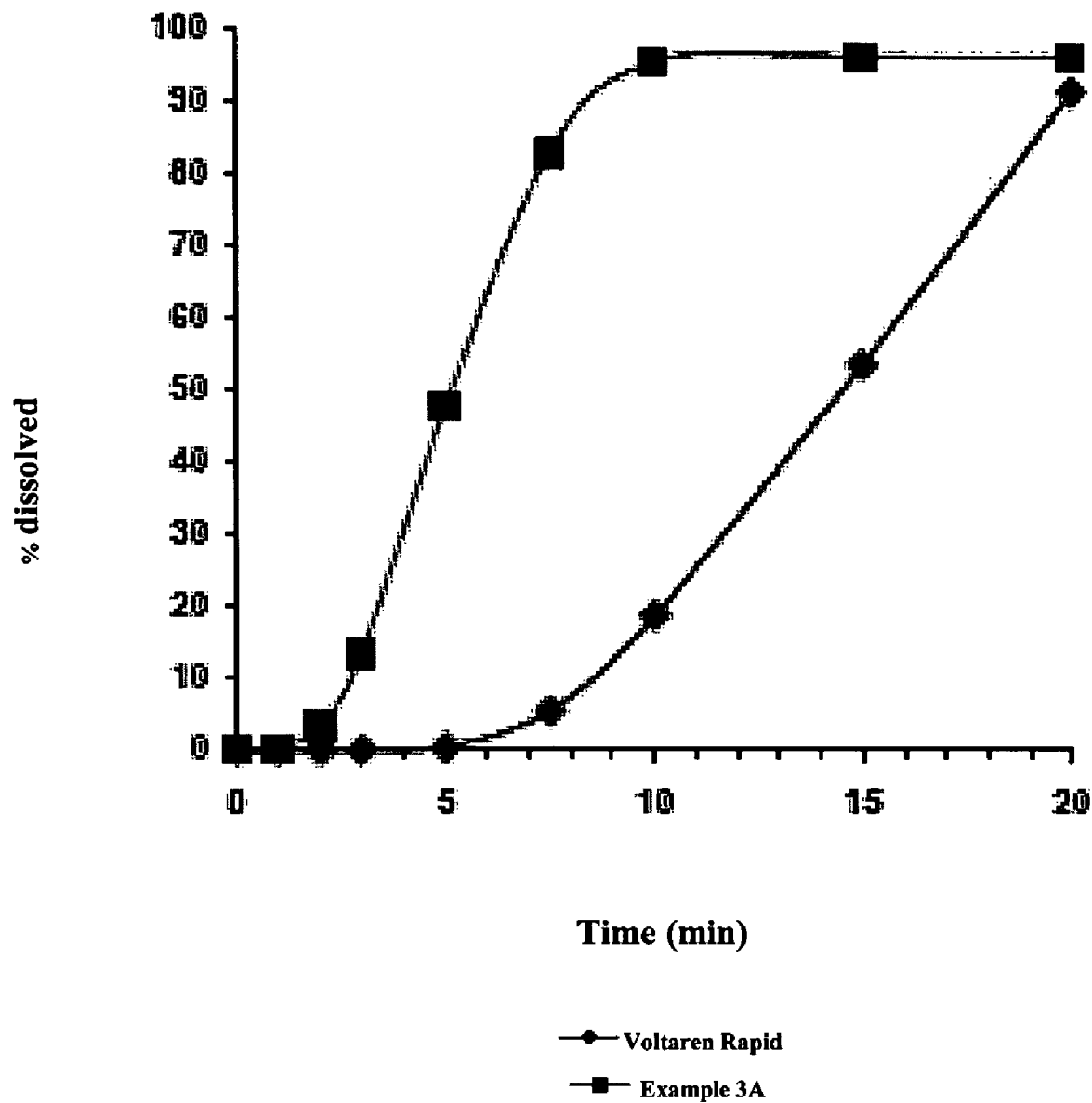
FIG. 1 is a graph depicting the dissolution profiles over time of two tablet formulations of 50 mg. diclofenac potassium, a tablet marketed commercially as Voltaren Rapide® (♦), and a tablet of the present invention having the formulation set forth in Table 8 (■).

As used in the specification and claims, the singular forms a, an and the include plural references unless the context clearly dictates otherwise. For example, the term a pharmaceutical excipient may refer to one or more pharmaceutical excipients for use in the presently disclosed formulations and methods.

USP means the United States Pharmacopeia and National Formulary (USP 28-NF 23). Rockville, Md.: United States Pharmacopeia Convention; 2004, unless stated to the contrary. USP 28<701> refers to physical test 701, disintegration, contained on pages 2411-2412 of the USP. USP 28 <711> refers to physical test 711, dissolution, contained on pages 2412-2414 of the USP.

A dosage form, as used herein, refers to a formulation that is ready for administration to a subject. As used herein, it specifically refers to solid dosage forms, including, but not limited to, tablets, powders and capsules, tablets being the most preferred. An "intact" dosage form refers to a dosage form which is ingested in the form it is provided. Intact dosage forms are therefore to be distinguished from orally disintegrating tablets which disintegrate in the mouth before being ingested or effervescent tablets which are dissolved in water before being ingested. In preferred embodiments of this invention, the dosage form is a tablet, and the tablets are ingested in an intact form.

$C_{max}$ refers to the maximum plasma concentration of a drug following oral administration of the solid oral dosage form to patients. Normalized $C_{max}$ refers to the value obtained by dividing $C_{max}$ into the dosage strength of the solid oral dosage form.

AUC refers to the area under the curve that tracks the plasma concentration (ng/ml) of a drug over a given time following the oral administration of the solid oral dosage form to patients. AUC can be measured from 0 to 12 hours or from 0 to 24 hrs following the administration and in these cases are referred to as AUC ((0-12)) or AUC ((0-24)), respectively.

Normalized AUC is obtained by dividing the AUC into the dosage strength of the solid oral dosage form of the drug. For example, if the AUC ((0-12)) is 160 hr·ng/ml following the oral administration of a solid oral dosage form containing 200 mg of active ingredient, the normalized AUC ((0-12)) is 0.8 hr·ng/ml/mg.

An excipient is considered "freely soluble" in the context of this application if the excipient meets the requirements for either "freely soluble" or "very soluble" excipients set forth in the United States Pharmacopeia. Therefore, an excipient that is "freely soluble" in water is an excipient for which 10 or fewer parts of water are required to dissolve one part of the excipient material at 20 degrees Celcius.

Diclofenac is chemically described as [(2,6-dichloroanilino)-2-phenyl]-2-acetic acid, and is represented by the following chemical structure:

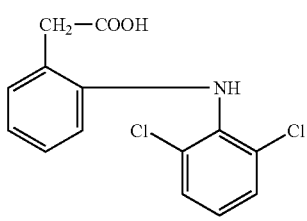

When used herein, the term diclofenac means the acetic acid form of diclofenac, and any of its pharmaceutically acceptable salts. Therefore, when a weight ratio is given, it will be understood that the ratio refers to the relative weight of diclofenac acid in the ratio, and the relative weight of diclofenac potassium (or other salt) in the ratio.

Acute pain conditions include pain that is temporary or passing, in contrast to chronic pain that is recurring or constant. Acute pain conditions thus include pain deriving from soft tissue disorders such as sprains and strains, soft tissue lacerations, migraine attacks, and other painful conditions such as renal colic, acute gout, dysmenorrhoea, and following invasive surgical procedures. While the invention is particularly useful in the treatment of acute pain, it will also be understood that the compositions of the present invention are also useful in chronic pain conditions. Examples of chronic pain conditions include rheumatoid arthritis, osteoarthritis, and ankylosing spondylitis; and periarticular disorders such as bursitis and tendonitis.

Discouraging Off-Label Use

In a first principal embodiment the invention provides a blister pack dosing regimen that (1) discourages the inappropriate use of acute pain medications for the treatment of chronic long-term pain, (2) provides convenient predictable dosing, and (3) enables the formulation of moisture sensitive and rapidly bioavailable dosage forms for treating acute pain. In this embodiment the invention provides a method of packaging an acute pain medication, preferably diclofenac potassium, to discourage its use in the treatment of chronic pain comprising: (a) formulating said drug in a rapidly bioavailable dosage form; and (b) packaging said drug in a blister package divided into from five to fourteen medication segments, wherein: (i) each medication segment corresponds to one day of treatment, and (ii) each medication segment is divided into from one to four unit doses corresponding to a daily dosage for said drug. The invention also relates to a method of using acute pain drugs that are packaged to discourage their off-label use, and thus also provides a method of treating acute pain comprising: (a) providing an acute pain medication, preferably a nonsteroidal anti-inflammatory drug, and even more preferably diclofenac or one of its pharmaceutically acceptable salts, in a dosage form that is characterized by: (i) an excipient base that provides rapid bioavailability; and (ii) blister packaging divided into from five to fourteen medication segments, wherein each medication segment corresponds to one day of treatment, and each medication segment is divided into from one to four unit doses corresponding to a daily dosage for said drug; and (b) administering said acute pain medication to a patient suffering from acute pain.

Various acute pain regimens can be implemented through the methods of the present invention. For example, the regimen will typically last from about 7 to about 14 days, and include from about 1 to about 6 pills per day. The packaging will thus typically comprise from about 7 to about 14 segments corresponding to individual days of treatment, and each segment will be divided into from 1 to 6 blister cavities representing the number of pills to be taken in a single day. There can be 5, 6, 7, 8, 9, 10, 11, 12, 13 or 14 medication segments on the card, containing 1, 2, 3, 4, 5, 6, 7 or 8 blister cavities in each segment. In a preferred embodiment, the card contains seven segments of medication and three blisters per segment.

The segments can be defined by physical characteristics of the package, such as perforations that divide the segments, scoring between segments, or by indicia printed on the package that delineate between the segments. The acute pain regimens of the present invention can employ practically any tablet or capsule dosage form, including effervescent tablets and ODTs, but in a preferred embodiment the regimens employ IR tablet dosage forms, and most preferably IR tablets that have been specially formulated for rapid bioavailability.

Various moisture resistant materials are known in the art for manufacturing blister packs, and any one of these materials could be used in the practice if the present invention. The optimum materials would, however, be almost practically impermeable to humidity, and would include materials such as an OPA-Alu-PVC blister. The blister packaging is preferably capable of preventing the dosage form from absorbing more than 4.0, 3.0, 2.0 or even 1.0 wt. % moisture in three months when stored at 40° C. and 75% relative humidity.

In addition, the blister packaging may be imprinted with indicia that distinguish between segments on the card, or that instruct the user on the proper use of the card. Other indicia may provide precautions which, for example, would discourage use of the drug for the treatment of chronic pain. For example, the precautions might state that the safety of the product has only been studied in short term studies, or that the safety of the drug during long term use has not been adequately investigated.

A preferred class of acute pain medications are non-steroidal anti-inflammatory drugs including, among others, fenamic acid derivatives, indene derivatives, and ibufenac derivatives. Csáky and Barnes in "Cutting's Handbook of Pharmacology," Appleton-Century-Crofts, Norwalk, CN (1984). Fenamic acid derivatives are broadly classified as o-anilino derivatives of benzoic, phenylacetic, and nicotinic acids and are defined by Csáky and Barnes as including flufenemic acid, mefenamic acid, meclofenamic acid, clonixeril, clonixin, flunixin, and diclofenac, including the pharmaceutically acceptable salts thereof. Indene derivatives generally are acetic acid, propionic acid, and benzoic acid derivatives containing a pyrrole (or a pyrazole, pyrroline or pyrrolidine) ring and are defined by Csáky and Barnes as including indomethacin, carprofen, etodolac, fendosal, indoprofen, prodolic acid, sermetacin, zidometacin, and zomeprirac, including the pharmaceutically acceptable salts thereof. Compounds not so classified by Csáky and Barnes but related in being acetic acid, propionic acid, or benzoic acid, derivatives and here so classified include tolmetin, sulinac, cicloprofen, and cinchophen, including the pharmaceutically acceptable salts thereof. Ibufenac derivatives are acetic and propionic acid derivatives bearing a substituted aromatic hydrocarbon ring, such as phenyl or naphthyl, and are defined by Csáky and Barnes as including iflunisal, fenoprofen, ibuprofen, naproxen, aldlofenac, amfenac, cliprofen, fenclofenac, fenclorac, fluprofen, ketoprofen, naproxol, fenbufen, and ibufenac, including the pharmaceutically acceptable salts thereof.

Diclofenac acid and its pharmaceutically acceptable salts are a particularly preferred acute pain medication, especially diclofenac potassium. Other pharmaceutically acceptable salts include those of sodium and other alkali and alkaline earth metals, or salts of organic nature, such as the salts of basic amino acids, such as lysine, arginine and omithine. In a preferred embodiment, 10-60 mg. or 50 mg. of diclofenac potassium is used in the final dosage form, although other amounts could be used including 12.5, 25, 37.5, 75 or 100 mg. The diclofenac preferably has a loss on drying of not less than 0.5%, and an average particle size of greater than 100 microns and less than 400 microns.

Rapidly Bioavailable Dosage Forms

The dosage forms used in this invention are preferably "rapidly bioavailable" in the sense that they are specially formulated to disintegrate/dissolve quickly when ingested into the stomach. Numerous means are available for promoting the disintegration or dissolution of diclofenac tablets or capsules, including, for example, the shell used for the capsule, formulation excipients such as disintegrants, pH buffers, effervescing agents, freely soluble excipients, hygroscopic excipients, surfactants, that promote the disintegration and dissolution of the dosage form and the active molecule, and counterions of the drug molecule. The dosage forms of the present invention are typically characterized by an inverse relationship between disintegration rate and moisture uptake. The hardness of the tablets is typically greater than about 4.1 kp, and more typically greater than about 6.0 or 8.0 kp.

Disintegration times for the dosage forms of the present invention, when tested according to USP 28<701>, are preferably less than about 20 minutes, 15 minutes, 10 minutes, 5 minutes, or even 4 minutes, and greater than about 1, 2 or 3 minutes, most preferably from about 3 to about 5 minutes. Dissolution times for the dosage forms of the present invention, when tested according to USP 28<711>, based on the time it takes to dissolve 90 or 95 wt. % of the drug substance, are preferably less than about 20 minutes, 15 minutes, 10 minutes, 5 minutes, or even 3 minutes, and greater than about 1 or 2 minutes. In a preferred embodiment, the dissolution profile for the dosage forms of the present invention is in accordance with the following specification: not less than 85, 90 or 95% dissolved after 15 minutes in simulated intestinal fluid (i.e. water) at pH=6.8

Mean $t_{max}$ attained by the dosage forms of the present invention is preferably less than about 40 minutes, 35 minutes, 30 minutes, 25 minutes or 20 minutes, and greater than about 5 minutes, 10 minutes or 15 minutes. Mean $t_{max}$ is preferably from about 5 to about 30 minutes, from about 10 to about 30 minutes, or from about 13 to about 27 minutes. The corresponding coefficient of variation is normally in the range of 70-90%, which means that the $T_{max}$ is strongly variable and dependent on the physical characteristics of the patient (Physicians' Desk Reference, 52 edition, 1998, pag. 1831)). The inter-subject coefficient of variability for said $t_{max}$ is preferably less than about 80, 75, 60, 50, 49, 46, 40, 35, 30% or 25%.

Figure 3:
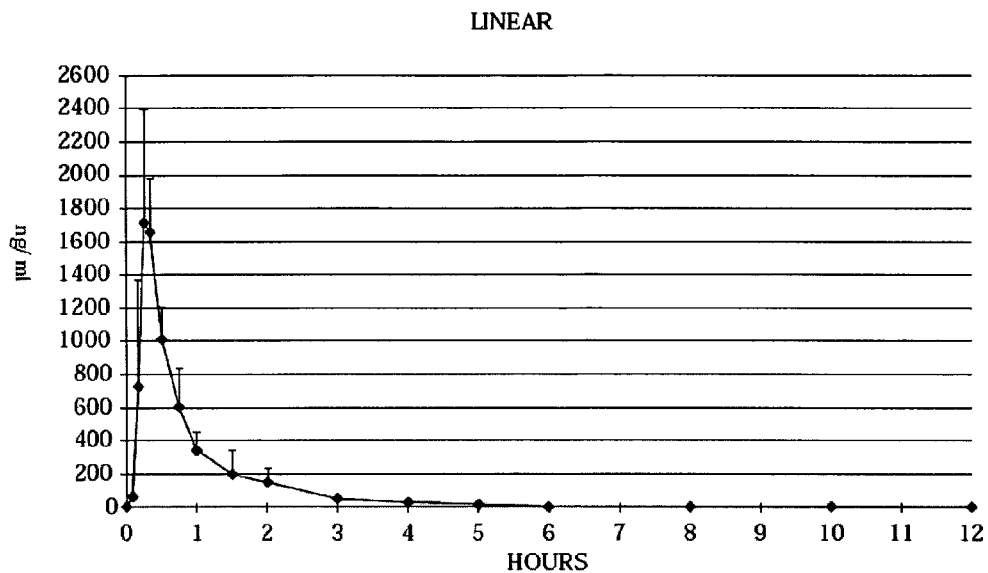
FIG. 3 is a graph depicting the mean plasma concentration of diclofenac over time in patients after oral administration of Tablet T1 of the present invention, wherein Tablet T1 is a tablet obtained by alcoholic granulation having the formulation set forth in Table 9.
Figure 4:
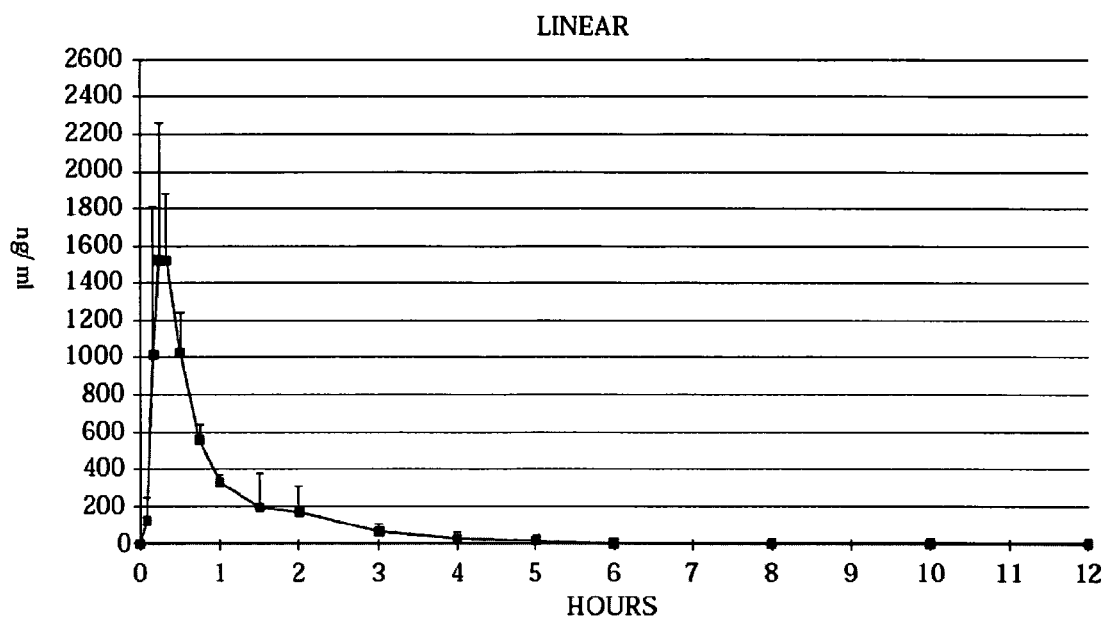
FIG. 4 is a graph depicting the mean plasma concentration of diclofenac over time in patients after oral administration of Tablet T2 of the present invention, wherein Tablet T2 is a tablet obtained by direct compression having the formulation set forth in Table 9.
Figure 5:
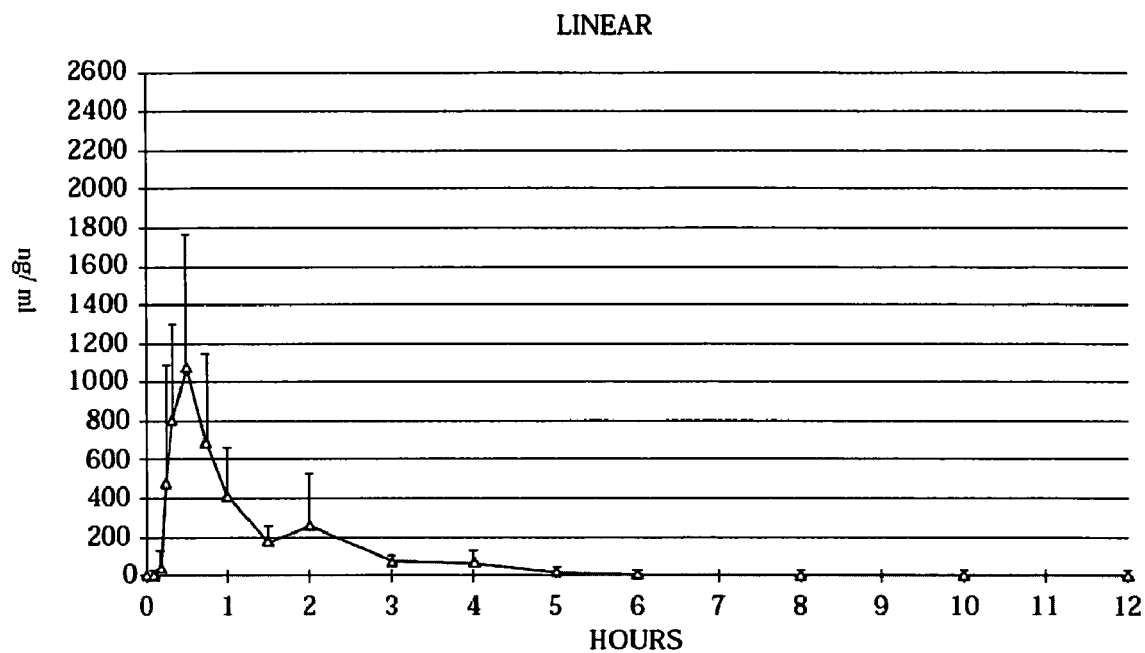
FIG. 5 is a graph depicting the mean plasma concentration of diclofenac over time in patients after oral administration of a 50 mg. diclofenac potassium tablet marketed commercially as Voltaren Rapide®.
Figure 6:
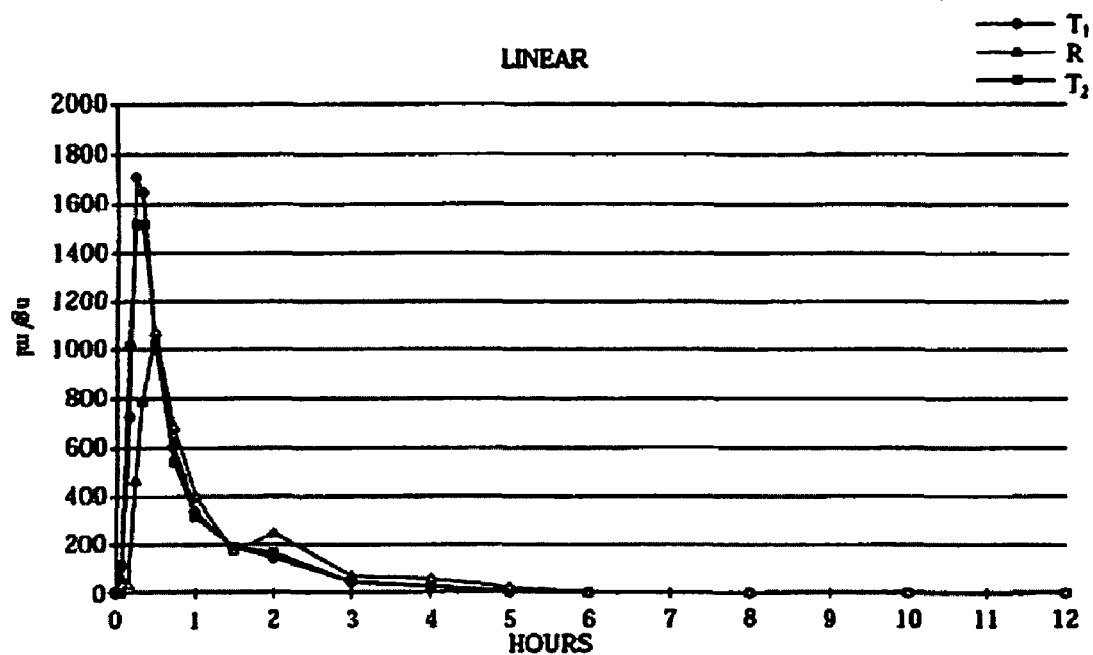
FIG. 6 is a composite overlay of the graphs contained in FIG. 3-5, and depicts the mean plasma concentration of diclofenac over time in patients after oral administration of Tablet T1 of the present invention, Tablet T2 of the present invention, and Voltaren Rapide®.

Mean $C_{max}$ attained by the formulations of the present invention is preferably greater than about 1400 ng/ml (0.028 liter$^{-1}$), 1500 ng/ml (0.03 liter$^{-1}$), 1600 ng/ml (0.032 liter $^{-1}$) or 1700 ng/ml (0.034 liter $^{-1}$), and less than about 2500 ng/ml (0.05 liter $^{-1}$) or 2300 ng/ml (0.046 liter $^{-1}$), for a 50 mg. formulation. A preferred range is 1500-2500, 1700-2500, or 1700-2300 ng/ml for a 50 mg. formulation. The inter-subject coefficient of variability for said $C_{max}$ preferably is less than about 70, 60, 50, 45 or 40%. In contrast to other commercially marketed diclofenac formulations, the formulations of the present invention preferably display only one meaningful peak blood concentration after ingestion. Compare FIGS. 3 and 4.

Preferred $C_{max}$ and $t_{max}$ ranges for various dosage forms of the invention are set forth below in Table A:

TABLE A

|  | Mean $C_{max}$ (ng/ml) | Mean $t_{max}$ (min) |
|---|---|---|
| 50 mg. diclofenac tablet or capsule | 1500-2100; 1750-2000; 1600-1900 | 5-35; 10-30; 12-25; 15-20 |
| 25 mg. diclofenac tablet or capsule | 700-1150; 750-950; 800-900; 850-1050; 900-1000 | 5-35; 10-30; 15-30; 15-25 |
| 12.5 mg. diclofenac tablet or capsule | 350-650; 400-600; 450-550 | 5-35; 10-30; 15-25 |

In one embodiment the rapid bioavailability is achieved by incorporating in the dosage form means for generating a gaseous and alkaline environment when orally ingested into the stomach. Suitable means for generating a gaseous and alkaline environment that is not harmful to the gastrointestinal mucosa include, but are not limited to, sodium carbonate, potassium carbonate, sodium bicarbonate, potassium bicarbonate, calcium carbonate, magnesium carbonate, sodium glycine carbonate, disodium hydrogen phosphate, sodium dihydrogen phosphate, and mixtures thereof. Suitable gas generating means are not limited to those which are based upon a reaction which forms carbon dioxide. Reactants which evolve oxygen or other gases and which are safe for human consumption are also considered within the scope of the present invention.

The dosage form also preferably includes a hygroscopic excipient which may double as the means for generating an alkaline and gaseous environment. Products that at relative humidity of 80% (RH=80%) and 25° C. demonstrate low water absorption ability (lower than 1% during 24 hrs) have a hygroscopic point below 80% (j<80% RH) and are not considered hygroscopic within the meaning of this invention. A hygroscopic excipient could thus have the ability to absorb greater than about 1 wt. %, 3 wt. %, 5 wt. % or 7 wt. % moisture within a twenty four hour period in a humidity chamber maintained at 80% RH and 25° C. Alternatively, a hygroscopic excipient could be defined as an excipient that is able to absorb greater than about 1 wt. %, 2 wt. %, 3 wt. % or 4 wt. % moisture within a twenty four hour period in a humidity chamber maintained at 60% RH and 25° C. Various hygroscopic excipients could be used in practicing the present invention, including various water-soluble hygroscopic polyhydroxy compounds or esters thereof such as glycerol and its mono- and diesters derived from low molecular weight carboxylic acids, e.g., monoacetin and diacetin (respectively, glyceryl monoacetate and glyceryl diacetate), ethylene glycol, diethylene glycol, triethylene glycol, 1,3-propanediol, trimethylolethane, trimethylolpropane, pentaerythritol, sorbitol, and the like. Other examples of hygroscopic or water-swellable materials include pharmaceutically acceptable disintegrants such as crosslinked polyvinylpyrrolidone, starch NF, and hygroscopic. In a preferred embodiment the hygroscopic excipient is potassium bicarbonate or sodium bicarbonate.

The means for generating a gaseous and alkaline environment and/or hygroscopic excipients are typically employed in a weight ratio relative to the diclofenac of greater than about 1:5, 2:5, 2:1, 3:1 or 5:1. If desired, an upper limit on the buffer: diclofenac ratio can be placed at about 20:1, 10:1, 5:1, 1:1, 4:5 or 3:5. Ranges can be selected from any two of the foregoing values that are mathematically possible. In a preferred embodiment, the buffer:diclofenac weight ratio ranges from about 1:5 to about 4:5. As a total percentage of the dosage form, the means for generating a gaseous and alkaline environment preferably makes up greater than about 5, 7 or 9 wt. % of the dosage form formulation, and less than about 25, 20 or 15 wt. % of the formulation. The means preferably yields a pH greater than about 7.0, 7.5, 7.8 or 8.0, and less than about 9.2, 9.0, 8.8 or 8.5 when the dosage form is mixed with 50 ml of water at 25 degrees Celsius. Alternatively, the means preferably yields a pH greater than about 6.8, 7.0, 7.2, or 7.5, and less than about 8.8, 8.5, 8.3 or 8.0 when the dosage form is mixed with 200 ml of water at 25 degrees Celsius.

Alternatively, the dosage form itself can be characterized by its hygroscopicity. In the present invention, dosage forms that at relative humidity of 80% (RH=80%) demonstrate low water absorption ability (lower than 1% during 24 hrs) have a hygroscopic point below 80% (j<80% RH) and are not hygroscopic at normal conditions. A hygroscopic dosage form could thus have the ability to absorb greater than about 1 wt. %, 1.25 wt. %, 1.5 wt. % or 2 wt. % moisture within a twenty four hour period in a humidity chamber maintained at 80% RH and 25° C. Alternatively, a hygroscopic dosage form could be defined as a dosage form that is able to absorb greater than about 0.50 wt. %, 0.75 wt. %, 1 wt. %, 1.25 wt. %, or 1.5 wt. % moisture within a twenty four hour period in a humidity chamber maintained at 60% RH and 25° C.

Tests performed on 50 mg. diclofenac potassium tablets of the present invention maintained at 25° C. and 60% RH over twenty four hours showed an increase in KF(% water) from 1.995% (at time zero) to 3.456% (after 24 hours). Tests performed on 50 mg. diclofenac potassium capsules of the present invention maintained at 25° C. and 60% RH over twenty four hours showed an increase in KF(% water) from 1.905% (at time zero) to 2.93% (after 24 hrs.). The final dosage form will not typically contain greater than about 5 wt. % water, initially or after 1, 2 or 3 years of storage.

The dosage form can also be formulated to be rapidly bioavailable by incorporating at least 20 wt. %, 30 wt. %, 40 wt. %, 50 wt. %, or 60 wt. % of excipients that are freely soluble in water. An excipient is considered freely soluble in the context of this application if 1 part of excipient is soluble in 1-10 parts of water at 20° C. Examples of freely soluble excipients include mannitol, dextrates (i.e. a purified mixture of saccharides resulting from the controlled enzymatic hydrolysis of starch), dextrin, dextrose, fructose, lactitol, lactose anhydrous, sorbitol, sucrose, and compressible sugar. Of these, mannitol and lactitol are particularly preferred due to their beneficial non-hygroscopic properties, which improves their processability and handling during the manufacturing process. In a preferred embodiment the dosage form will comprise from about 30 to about 80 wt. % of the combined hygroscopic diluent and freely soluble diluent, from about 35 to about 75 wt. % of the combined hygroscopic diluent and freely soluble diluent, or from about from about 40 to about 70 wt. % of the combined hygroscopic diluent and freely soluble diluent. In addition, the hygroscopic diluent and freely soluble excipient will preferably be present in a weight ratio of from about 1:20 to about 5:1, from about 1:10 to about 3:1, from about 1:8 to about 1:1, from about 1:8 to about 1:2, or from about 1:4 to about 1:1.

Yet another way to render the dosage forms rapidly bioavailable is to incorporate a surfactant that aids in the solubility of the dosage form, such as sodium lauryl sulfate. Preferred surfactants will have an HLB value of at least 10 or 12, and preferably at least about 14 or 15. An upper bound can also be placed on the HLB of the surfactant, preferably of 60, 50 or 40. In certain preferred embodiments, the HLB value of the surfactant is from about 15 to 60, and in further embodiments the HLB is most preferably from about 20 to about 50. Suitable pharmaceutically-acceptable anionic surfactants include, for example, those containing carboxylate, sulfonate, and sulfate ions. The most common cations associated with these surfactants are sodium, potassium, ammonium and triethanolamine. The chain length of the fatty acids typically range from 12 to 18. Although a large number of alkyl sulfates are available as surfactants, one particularly preferred surfactant is sodium lauryl sulfate, which has an HLB value of about 40. Other suitable wetting agents include glyceryl monooleate, sorbitan ester, docusate sodium, and cetrimide.

EXAMPLES

Example 1

Tablet Core Formulations

Uncoated diclofenac tablets containing 50 mg. of diclofenac potassium were prepared based on the formulations given in Table 1 below. Formulations were prepared using alcoholic granulation (Tablet C) and direct compression (Tablet B).

TABLE 1

| Names of ingredients | Tablet C (alcoholic granulation) | Tablet B (direct compression) | Function | Standard |
|---|---|---|---|---|
| Active ingredients | | | | |
| Diclofenac potassium | 50 mg.* | 50 mg | Active ingredient | Eur. Ph. |
| Tablet cores excipients | | | | |
| Potassium hydrogen carbonate | 22 | 22 | Buffering agent | Eur. Ph. |
| Mannitol | 50 | 119.9 | Diluent and disintegrating agent | Eur. Ph. |
| Maize starch | 25 | / | Binder diluent | Eur. Ph. |
| Methocel A4C | 0.2 | / | Thickener | Eur. Ph. |
| Crospovidone | 1.0 | 6.0 | Binder | Eur. Ph. |
| Sodium lauryl sulphate | 0.1 | 0.1 | Solubilizing agent | Eur. Ph. |
| Magnesium stearate | 4.5 | 2.0 | Lubricant agent | Eur. Ph. |
| Ultramyl | 2.5 | / | Lubricant agent | Eur. Ph. |
| Aerosil | 1.0 | / | Lubricant agent | Eur. Ph. |
| Total weight | 156.3 | 200.0 mg | | |

*Units are in milligrams unless otherwise specified.

Example 2

Stability Testing

Stability tests were conducted in various blister packaging materials on the tablet cores (Tablet B and Tablet C), and on Tablet B tablets coated with an aqueous polymer coating suspension (Tablet BA) and an alcoholic polymer coating solution (Tablet BB). Stability testing was restricted to three different blister types. The properties of the forming and lidding films used in the three blister materials tested are as follows:

PVDC-coated PVC and hard aluminum (25 μm, coated on the underside with a vinyl lacquer) are the materials of the forming film and the lidding part of the tested blister 1, respectively. The thickness of the PVDC coat is 40 μm while that of the PVC film is 250 μm.

PVDC-coated PVC and hard aluminum (25 μm, coated on the underside with a vinyl lacquer) are the materials of the forming film and the lidding part of the tested blister 2, respectively. The thickness of the PVDC coat is 80 μm while that of the PVC film is 250 μm.

OPA/Al/PVC and hard aluminum (25 μm, coated on the underside with a vinyl lacquer) are the materials of the forming film and the lidding part of the tested blister 3, respectively. Nylon (Oriented Polyamide)-Aluminum-PVC (OPA/Al/PVC) is a laminate, which consists of 25 μm OPA/45 μm aluminum/60 μm PVC.

An appropriate quantity of tablet cores (Tablets B and C) and coated tablets (Tablets BA and BB), in original packaging (blisters 1-3) was stored in Weiss-Enet climatic chambers for six months under the following conditions of temperature and relative humidity:

| Temperature (° C.) | Relative humidity (±1%) |
|---|---|
| 25 | 60 |
| 30 | 60 |
| 40 | 75 |

Samples were withdrawn at suitable intervals and subjected to testing for Diameter, Thickness, Hardness, Weight, Disintegration time in water (37° C.), Water content, Dissolution buffered pH 7.5 medium, and Assay. The measurements were performed on six tablet cores or coated tablets taken at random in all instances, and the average values were recorded. The results are given in Tables 2-7 below.

TABLE 2

Influence of packaging material (blisters 1, 2 and 3) on the stability of Tablets B and C stored at 25° C. (RH = 60%)[a]

| Tests | Tablet B[b] Time zero | Tablet B Blister 1[c] 3 months | Tablet B Blister 1[c] 6 months | Tablet B Blister 2 3 months | Tablet B Blister 2 6 months | Tablet B Blister 3 3 months | Tablet B Blister 3 6 months |
|---|---|---|---|---|---|---|---|
| Diameter[f] (mm) | 7.0 | 7.0 | / | 7.1 | 7.1 | 7.0 | 7.1 |
| Thickness[f] (mm) | 4.4 | 4.4 | / | 4.4 | 4.5 | 4.4 | 4.4 |
| Hardness[f] (N) | 71 | 65 | / | 65 | 63 | 71 | 74 |
| Weight (mg) | 198 | 201 | / | 200 | 199 | 199 | 198 |
| Water content[g] (%) | 2.4 | 3.2 | / | 2.8 | 2.7 | 2.6 | 2.5 |
| Disintegration time[h] (min.:sec.) | 2:50 | 6:12 | / | 3:43 | 3:56 | 2:33 | 2:33 |
| Dissolution[i] after 20 min. (%) | 93 | 96 | / | 98 | 96 | 95 | 99 |
| Assay[j] (%) | 96.6 | 95.6 | / | 96.0 | 96.2 | 99.8 | 99.0 |

| Tests | Tablet C[d] Time zero | Tablet C Blister 1[c,e] 3 months | Tablet C Blister 1[c,e] 6 months | Tablet C Blister 2[e] 3 months | Tablet C Blister 2[e] 6 months | Tablet C Blister 3[e] 3 months | Tablet C Blister 3[e] 6 months |
|---|---|---|---|---|---|---|---|
| Diameter[f] (mm) | 7.0 | 7.0 | / | 7.0 | / | 7.0 | / |
| Thickness[f] (mm) | 3.5 | 3.6 | / | 3.5 | / | 3.5 | / |
| Hardness[f] (N) | 31 | 24 | / | 25 | / | 32 | / |
| Weight (mg) | 154 | 157 | / | 155 | / | 155 | / |
| Water content[g] (%) | 3.5 | 3.5 | / | 5.0 | / | 4.2 | / |
| Disintegration time[h] (min.:sec.) | 3:05 | 2:28 | / | 2:23 | / | 2:12 | / |
| Dissolution[i] after 20 min. (%) | 95 | 96 | / | 98 | / | 97 | / |
| Assay[j] (%) | 97.0 | 96.4 | / | 97.8 | / | 99.2 | / |

[a] All values are average values determined on six units taken at random.
[b] Matrix tablets produced by direct compression of the mixture F11 with a rotary tablet machine.
[c] Stability in blister 1 was interrupted after 3 months.
[d] Matrix tablets produced from the mixture F3 (alcoholic granulation) with a rotary tablet machine.
[e] Stability of batch no. 990310C was interrupted after 3 months.
[f] Erweka TBH 30 HD apparatus.
[g] Determined according to Eur. Ph. (Karl Fischer semi-micro water determination).
[h] Determined in water (37° C.) according to Eur. Ph..
[i] Determined in buffered pH 7.5 medium according to Eur. Ph..
[j] Determined by high performance liquid chromatography (HPLC).

TABLE 3

Influence of packaging material (blisters 1, 2 and 3) on the stability of Tablets B and C stored at 30° C. (RH = 60%)[a]

| Tests | Tablet B[b] Time zero | Tablet B Blister 1[c] 3 months | Tablet B Blister 1[c] 6 months | Tablet B Blister 2 3 months | Tablet B Blister 2 6 months | Tablet B Blister 3 3 months | Tablet B Blister 3 6 months |
|---|---|---|---|---|---|---|---|
| Diameter[f] (mm) | 7.0 | 7.1 | / | 7.1 | 7.1 | 7.1 | 7.1 |
| Thickness[f] (mm) | 4.4 | 4.5 | / | 4.5 | 4.5 | 4.4 | 4.5 |
| Hardness[f] (N) | 71 | 66 | / | 60 | 64 | 72 | 71 |
| Weight (mg) | 198 | 202 | / | 200 | 202 | 199 | 199 |
| Water content[g] (%) | 2.4 | 6.4 | / | 3.6 | 3.1 | 2.2 | 2.5 |
| Disintegration time[h] (min.:sec.) | 2:50 | 5:32 | / | 5:09 | 5:49 | 2:40 | 2:30 |
| Dissolution[i] after 20 min. (%) | 93 | 95 | / | 94 | 95 | 93 | 96 |
| Assay[j] (%) | 96.6 | 94.2 | / | 95.4 | 96.0 | 96.0 | 96.4 |

| Tests | Tablet C[d] Time zero | Tablet C Blister 1[c,e] 3 months | Tablet C Blister 1[c,e] 6 months | Tablet C Blister 2[e] 3 months | Tablet C Blister 2[e] 6 months | Tablet C Blister 3[e] 3 months | Tablet C Blister 3[e] 6 months |
|---|---|---|---|---|---|---|---|
| Diameter[f] (mm) | 7.0 | 7.1 | / | 7.0 | / | 7.0 | / |
| Thickness[f] (mm) | 3.5 | 3.6 | / | 3.6 | / | 3.4 | / |
| Hardness[f] (N) | 31 | 24 | / | 27 | / | 31 | / |
| Weight (mg) | 154 | 158 | / | 157 | / | 154 | / |
| Water content[g] (%) | 3.5 | 6.4 | / | 5.7 | / | 4.0 | / |
| Disintegration time[h] (min.:sec.) | 3:05 | 2:17 | / | 2:09 | / | 2:35 | / |
| Dissolution[i] after 20 min. (%) | 95 | 97 | / | 96 | / | 98 | / |
| Assay[j] (%) | 97.0 | 97.2 | / | 97.2 | / | 100.0 | / |

TABLE 4

Influence of packaging material (blisters 1, 2 and 3) on the stability of Tablets B and C stored at 40° C. (RH = 75%)[a]

| Tests | Tablet B[b] Time zero | Tablet B Blister 1[c] 3 months | Tablet B Blister 1[c] 6 months | Tablet B Blister 2 3 months | Tablet B Blister 2 6 months | Tablet B Blister 3 3 months | Tablet B Blister 3 6 months |
|---|---|---|---|---|---|---|---|
| Diameter[f] (mm) | 7.0 | 7.2 | / | 7.1 | 7.1 | 7.0 | 7.1 |
| Thickness[f] (mm) | 4.4 | 4.5 | / | 4.5 | 4.6 | 4.6 | 4.4 |
| Hardness[f] (N) | 71 | 64 | / | 67 | 62 | 71 | 70 |
| Weight (mg) | 198 | 205 | / | 201 | 205 | 198 | 200 |
| Water content[g] (%) | 2.4 | 5.3 | / | 3.6 | 5.2 | 2.1 | 2.2 |
| Disintegration time[h] (min.:sec.) | 2:50 | 7:20 | / | 6:16 | 6:12 | 3:17 | 3:31 |
| Dissolution[i] after 20 min. (%) | 93 | 92 | / | 95 | 96 | 94 | 95 |
| Assay[j] (%) | 96.6 | 92.6 | / | 92.6 | 92.2 | 96.0 | 96.3 |

| Tests | Tablet C[d] Time zero | Tablet C Blister 1[c,e] 3 months | Tablet C Blister 1[c,e] 6 months | Tablet C Blister 2[e] 3 months | Tablet C Blister 2[e] 6 months | Tablet C Blister 3[e] 3 months | Tablet C Blister 3[e] 6 months |
|---|---|---|---|---|---|---|---|
| Diameter[f] (mm) | 7.0 | 7.1 | / | 7.0 | / | 7.0 | / |
| Thickness[f] (mm) | 3.5 | 3.7 | / | 3.6 | / | 3.5 | / |
| Hardness[f] (N) | 31 | 23 | / | 27 | / | 30 | / |
| Weight (mg) | 154 | 161 | / | 158 | / | 154 | / |
| Water content[g] (%) | 3.5 | 7.3 | / | 6.2 | / | 4.0 | / |
| Disintegration time[h] (min.:sec.) | 3:05 | 2:27 | / | 2:28 | / | 2:23 | / |
| Dissolution[i] after 20 min. (%) | 95 | 92 | / | 95 | / | 94 | / |
| Assay[j] (%) | 97.0 | 97.2 | / | 96.4 | / | 99.4 | / |

TABLE 5

Influence of packaging material (blisters 1, 2 and 3) on the stability of film-coated Tablets BA and BB stored at 25° C. (RH = 60%)[a]

| Tests | Tablet BA[b] Time zero | Tablet BA Blister 1[c] 3 months | Tablet BA Blister 1[c] 6 months | Tablet BA Blister 2 3 months | Tablet BA Blister 2 6 months | Tablet BA Blister 3 3 months | Tablet BA Blister 3 6 months |
|---|---|---|---|---|---|---|---|
| Diameter[f] (mm) | 7.1 | 7.1 | / | 7.1 | 7.1 | 7.1 | 7.2 |
| Thickness[f] (mm) | 4.6 | 4.6 | / | 4.5 | 4.6 | 4.5 | 4.5 |
| Hardness[f] (N) | 128 | 116 | / | 108 | 103 | 127 | 130 |
| Weight (mg) | 204 | 206 | / | 204 | 205 | 204 | 204 |
| Water content[g] (%) | 2.5 | 4.4 | / | 2.9 | 3.0 | 2.1 | 3.2 |
| Disintegration time[h] (min.:sec.) | 3:23 | 6:15 | / | 4:28 | 4:42 | 3:24 | 4:28 |

TABLE 5-continued

Influence of packaging material (blisters 1, 2 and 3) on the stability of film-coated Tablets BA and BB stored at 25° C. (RH = 60%)[a]

|  |  |  |  |  |  |  |  |
|---|---|---|---|---|---|---|---|
| Dissolution[i] after 20 min. (%) | 93 | 95 | / | 96 | 98 | 94 | 95 |
| Assay[j] (%) | 95.8 | 95.0 | / | 96.0 | 96.3 | 98.4 | 98.7 |

|  | Tablet BB[d] | Tablet BB Blister 1[e] | | Tablet BB Blister 2 | | Tablet BB Blister 3 | |
|---|---|---|---|---|---|---|---|
| Tests | Time zero | 3 months | 6 months | 3 months | 6 months | 3 months | 6 months |
| Diameter[f] (mm) | 7.1 | 7.1 | / | 7.1 | 7.2 | 7.1 | 7.2 |
| Thickness[f] (mm) | 4.5 | 4.6 | / | 4.5 | 4.7 | 4.5 | 4.5 |
| Hardness[f] (N) | 114 | 108 | / | 112 | 95 | 114 | 116 |
| Weight (mg) | 203 | 207 | / | 204 | 211 | 203 | 204 |
| Water content[g] (%) | 2.3 | 3.5 | / | 2.8 | 3.1 | 2.3 | 3.0 |
| Disintegration time[h] (min.:sec.) | 3:26 | 7:00 | / | 4:09 | 9:02 | 3:13 | 4:12 |
| Dissolution[i] after 20 min. (%) | 96 | 93 | / | 94 | 94 | 97 | 96 |
| Assay[j] (%) | 95.6 | 93.4 | / | 94.4 | 94.0 | 96.4 | 96.8 |

TABLE 6

Influence of packaging material (blisters 1, 2 and 3) on the stability of film-coated Tablets BA and BB stored at 30° C. (RH = 60%)[a]

|  | Tablet BA[b] | Tablet BA Blister 1[c] | | Tablet BA Blister 2 | | Tablet BA Blister 3 | |
|---|---|---|---|---|---|---|---|
| Tests | Time zero | 3 months | 6 months | 3 months | 6 months | 3 months | 6 months |
| Diameter[f] (mm) | 7.1 | 7.1 | / | 7.1 | 7.1 | 7.1 | 7.1 |
| Thickness[f] (mm) | 4.6 | 4.6 | / | 4.5 | 4.6 | 4.5 | 4.5 |
| Hardness[f] (N) | 128 | 103 | / | 110 | 110 | 130 | 128 |
| Weight (mg) | 204 | 206 | / | 205 | 206 | 204 | 203 |
| Water content[g] (%) | 2.5 | 5.5 | / | 3.1 | 3.6 | 2.2 | 3.0 |
| Disintegration time[h] (min.:sec.) | 3:23 | 5:59 | / | 4:33 | 6.11 | 3:39 | 3:51 |
| Dissolution[i] after 20 mm. (%) | 93 | 95 | / | 96 | 95 | 94 | 97 |
| Assay[j] (%) | 95.8 | 94.8 | / | 94.4 | 96.8 | 96.8 | 98.2 |

|  | Tablet BB[d] | Tablet BB Blister 1[e] | | Tablet BB Blister 2 | | Tablet BB Blister 3 | |
|---|---|---|---|---|---|---|---|
| Tests | Time zero | 3 months | 6 months | 3 months | 6 months | 3 months | 6 months |
| Diameter[f] (mm) | 7.1 | 7.1 | / | 7.1 | 7.1 | 7.1 | 7.1 |
| Thickness[f] (mm) | 4.5 | 4.6 | / | 4.5 | 4.6 | 4.3 | 4.6 |
| Hardness[f] (N) | 114 | 99 | / | 104 | 100 | 112 | 114 |
| Weight (mg) | 203 | 207 | / | 206 | 206 | 203 | 203 |
| Water content[g] (%) | 2.3 | 4.1 | / | 3.2 | 3.8 | 3.3 | 2.6 |
| Disintegration time[h] (min.:sec.) | 3:26 | 5:54 | / | 6:29 | 5:22 | 3:40 | 4:00 |
| Dissolution[i] after 20 mm. (%) | 96 | 94 | / | 96 | 93 | 93 | 96 |
| Assay[j] (%) | 95.6 | 94.6 | / | 94.0 | 98.5 | 97.8 | 97.0 |

TABLE 7

Influence of packaging material (blisters 1, 2 and 3) on the stability of film-coated Tablets BA and BB stored at 40° C. (RH = 75%)[a]

|  | Tablet BA[b] | Tablet BA Blister 1[c] | | Tablet BA Blister 2 | | Tablet BA Blister 3 | |
|---|---|---|---|---|---|---|---|
| Tests | Time zero | 3 months | 6 months | 3 months | 6 months | 3 months | 6 months |
| Diameter[f] (mm) | 7.1 | 7.1 | / | 7.2 | 7.2 | 7.1 | 7.1 |
| Thickness[f] (mm) | 4.6 | 4.6 | / | 4.6 | 4.7 | 4.5 | 4.6 |
| Hardness[f] (N) | 128 | 102 | / | 110 | 104 | 130 | 125 |
| Weight (mg) | 204 | 209 | / | 207 | 210 | 204 | 204 |
| Water content[g] (%) | 2.5 | 5.3 | / | 4.2 | 5.0 | 2.2 | 2.7 |
| Disintegration time[h] (min.:sec.) | 3:23 | 7:18 | / | 6:51 | 6:48 | 3:50 | 3:30 |

TABLE 7-continued

Influence of packaging material (blisters 1, 2 and 3) on the stability
of film-coated Tablets BA and BB stored at 40° C. (RH = 75%)[a]

| | | | | | | | |
|---|---|---|---|---|---|---|---|
| Dissolution[i] after 20 min. (%) | 93 | 93 | / | 94 | 96 | 95 | 96 |
| Assay[j] (%) | 95.8 | 95.0 | / | 95.4 | 98.1 | 98.2 | 96.3 |

| | Tablet BB[d] | Tablet BB Blister 1[e] | | Tablet BB Blister 2 | | Tablet BB Blister 3 | |
|---|---|---|---|---|---|---|---|
| Tests | Time zero | 3 months | 6 months | 3 months | 6 months | 3 months | 6 months |
| Diameter[f] (mm) | 7.1 | 7.2 | / | 7.1 | 7.1 | 7.1 | 7.1 |
| Thickness[f] (mm) | 4.5 | 4.6 | / | 4.6 | 4.6 | 4.5 | 4.6 |
| Hardness[f] (N) | 114 | 93 | / | 102 | 99 | 115 | 111 |
| Weight (mg) | 203 | 210 | / | 208 | 204 | 204 | 203 |
| Water content[g] (%) | 2.3 | 5.2 | / | 4.2 | 5.6 | 3.1 | 3.6 |
| Disintegration time[h] (min.:sec.) | 3:26 | 9:16 | / | 6:45 | 4:18 | 4:15 | 3:16 |
| Dissolution[i] after 20 min. (%) | 96 | 94 | / | 95 | 96 | 97 | 96 |
| Assay[j] (%) | 95.6 | 94.0 | / | 95.6 | 96.7 | 98.0 | 95.2 |

Example 3

Diclofenac K Tablet Dissolution Profile Comparison

Figure 2:
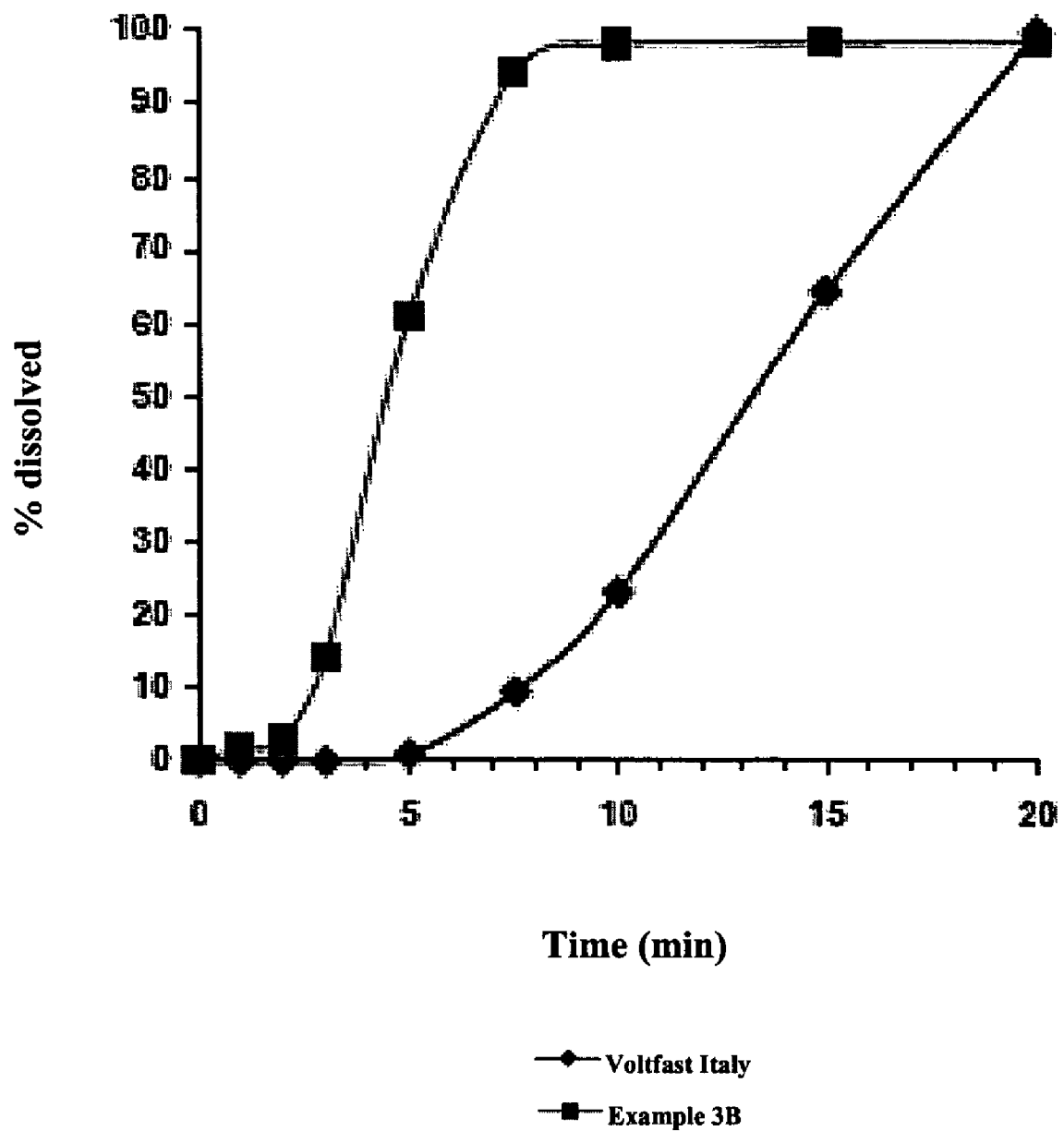
FIG. 2 is a graph depicting the dissolution profiles over time of two tablet formulations of 50 mg. diclofenac potassium, a tablet marketed commercially as Voltfast® (♦), and a tablet of the present invention having the formulation set forth in Table 8 (■).

Using the dissolution test procedure described in the European Pharmacopeia, the dissolution profiles for two tablets (Ex. 3a and 3b) having the composition set forth in Table 8 were generated. The only difference between the two tablets was the source of the diclofenac potassium. Dissolution profiles of 50 mg. diclofenac potassium tablets marketed as Voltaren Rapid and Voltfast were also generated, and graphs of the contrasting dissolution profiles were superimposed, to produce FIGS. 1 and 2 hereto.

TABLE 8

Composition of Test Formulations

| Names of Ingredients | Unit (mg.) | Function | Reference to Standards |
|---|---|---|---|
| Drug Substance | | | |
| Diclofenac Potassium | 50.0 | Anti-inflammatory agent | Eur. Ph. |
| Matrix Tablet Excipients | | | |
| Potassium Bicarbonate | 22.0 | Buffering Agent | Eur. Ph. |
| Mannitol | 116.4 | Diluent and Disintegrant Agent | Eur. Ph. |
| Sodium Lauryl Sulfate | 0.1 | Solubilizing Agent | Eur. Ph. |
| Macrogols (as Macrogol 6000) | 1.5 | Lubricant Agent | Eur. Ph. |
| Crospovidone | 6.0 | Binder | Eur. Ph. |
| Magnesium Stearate | 4.0 | Lubricant Agent | Eur. Ph. |

TABLE 8-continued

Composition of Test Formulations

| Names of Ingredients | Unit (mg.) | Function | Reference to Standards |
|---|---|---|---|
| Film-Coating Excipients | | | |
| Clear Opadry | | Coating Agent | In House Specifications |
| Total Weight | 204.0 | | |

Example 4

Diclofenac K Tablet Pharmacokinetic Profile Comparison

A further comparative test was carried out on immediate release formulations T1 and T2, as reported below in Table 9. A comparative bioavailabilty study was carried out on 6 healthy volunteers of both sexes in order to evaluate the in vivo results of the pharmacokinetic profiles of the present formulations if compared to those of a bioequivalent fast release formulation such as Voltaren Rapid® (50 mg of diclofenac potassium), by Novartis. The results, which are reported in FIGS. 3-6 are also in this case excellent: the $T_{max}$ is in fact prompter with the present formulations (T1=18.6 min, T2=16.8 min vs R1 40.8 min) and the $C_{max}$ is higher (T1=1878.3 ng/ml and T2=1744.8 ng/ml vs R1 1307 ng/ml); furthermore, also in this case the $T_{max}$ of both present formulations shows a coefficient of variation lower than reference formulation (T1=12.9% and T2=25% vs R1=95.6%).

TABLE 9

Formulation of Comparison Tablets

| | T1, K salt, 50 mg, tablets | T2, K salt, 50 mg, tablets Description | Reference, K salt, 50 mg, Voltaren ® Rapid tablets |
|---|---|---|---|
| Description | Diclofenac potassium 50 mg film-coated tablets (by alcoholic granulation) | Diclofenac potassium 50 mg film-coated tablets (by direct compression) | Diclofenac potassium 50 mg film-coated tablets |
| Active ingredient Excipients | Diclofenac potassium mg 50 Potassium bicarbonate mg 22 Mannitol mg 50 Maize starch mg 25 Hydroxypropylmethylcellulose mg 0.2 | Diclofenac potassium mg 50 Potassium bicarbonate mg 22 Mannitol 400 mg 119.9 | Diclofenac potassium mg 50 Calcium phosphate Saccharose Maize starch Talc |

TABLE 9-continued

Formulation of Comparison Tablets

| | T1, K salt, 50 mg, tablets | T2, K salt, 50 mg, tablets | Reference, K salt, 50 mg, Voltaren ® Rapid tablets |
|---|---|---|---|
| | | Description | |
| Description | Diclofenac potassium 50 mg film-coated tablets (by alcoholic granulation) | Diclofenac potassium 50 mg film-coated tablets (by direct compression) | Diclofenac potassium 50 mg film-coated tablets |
| | Sodium laurylsulfate mg 0.1 Polyvinylpyrrolidone mg 1 Sodium starch glycollate mg 2.5 Magnesium stearate mg 4.5 Silicium aerosil FK 160 mg 1 Coating Opadry Clear (HPMC 2910 and polyethyleneglycol 400) mg 4 | Sodium laurylsulfate mg 0.1 Polyvinylpyrrolidone mg 6 Magnesium stearate mg 2 Film Coating Opadry Clear (HPMC 2910, polyethyleneglycol 400) mg 4 | Sodium carboxymethylcellulose Colloidal anhydrous silicium Polyvinylpyrrolidone Microcrystalline cellulose Magnesium stearate Polyethylenglycole Titanidioxide (E171) Iron oxide red (E172) |
| Total weight | 160.3 mg | 204 mg | |

TABLE 10

Pharmacokinetics of Comparison Tablets.

| | | PK results | | |
|---|---|---|---|---|
| | | Test 1 (K, tablets 50 mg) | Test 2 (K, tablets 50 mg) | Reference (K, tablets 50 mg) |
| $C_{max}$ | Mean | 1873.30 | 1744.8 | 1307.0 |
| | SD | 553.80 | 572.3 | 558.4 |
| | CV % | 29.5 | 32.8 | 42.7 |
| | Min | 1228.9 | 1057.4 | 581.8 |
| | Max | 2516.5 | 2468.9 | 1935.5 |
| AUC | Mean | 1219 | 1237 | 1168 |
| | SD | 246 | 276 | 282 |
| | CV % | 20.2 | 22.3 | 24.1 |
| | Min | 874 | 848 | 913 |
| | Max | 1615 | 1668 | 1642 |
| $t_{max}$ | Mean | 0.31 h (18.6 min) | 0.28 h (16.8 min) | 0.68 h (40.8 min) |
| | SD | 0.04 | 0.07 | 0.65 |
| | CV % | 12.9 | 25.0 | 95.6 |
| | Min | 0.25 h (15 min) | 0.17 h (10.2 min) | 0.25 h (15 min) |
| | Max | 0.33 h (19.8 min) | 0.33 h (19.8 min) | 2.00 h (120 min) |

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of packaging a rapidly bioavailable diclofenac dosage form demonstrated to have a mean time to maximum plasma concentration ($t_{max}$) of from about 5 to about 40 minutes to discourage its administration in the treatment of chronic pain comprising:
   a) formulating diclofenac or a pharmaceutically acceptable salt thereof in a rapidly bioavailable tablet dosage form comprising an excipient base; and
   b) packaging said drug in a blister package divided into from five to fourteen medication segments, wherein:
      i) each medication segment corresponds to one day of treatment,
      ii) each medication segment is divided into from one to four unit doses corresponding to a daily dosage for said drug, and
      iii) said blister package is imprinted with indicia that distinguishes between said medication segments and instructs on the proper treatment with said drug;
   wherein said dosage form comprises from alkali metal carbonate or bicarbonate at a weight ratio to said diclofenac of from about 1:5 to about 4:5.

2. The method of claim 1 wherein said blister package prevents said dosage form from absorbing more than 4 wt. % moisture in three months when stored at 40° C. and 75% relative humidity.

3. The method of claim 1 wherein said dosage form comprises about 50 mg. of diclofenac potassium.

4. The method of claim 1 wherein said dosage form has been demonstrated to have a $t_{max}$ of from about 5 to about 30 minutes, and a mean maximum plasma concentration ($C_{max}$) of from about 1700 to about 2300 ng/ml.

5. The method of claim 1 wherein said dosage form has been demonstrated to have a $t_{max}$ of from about 5 to about 30 minutes, and a mean maximum plasma concentration ($C_{max}$) of from about 1500 to about 2500 ng/ml wherein said $t_{max}$ exhibits an inter-subject variability of less than about 49%.

6. The method of claim 1 wherein said dosage form has been demonstrated to yield one mean maximum plasma concentration ($C_{max}$) peak when orally ingested.

7. The method of claim 1 wherein said dosage form comprises from about 7 to about 20 wt. % of a hygroscopic excipient, having a hygroscopicity of greater than about 1 wt. % water absorption within a twenty four hour period in a humidity chamber maintained at 80% RH and 25 degrees Celcius.

8. The method of claim 1 wherein said dosage form comprises at least 20 wt. % of excipients that are freely soluble in water.

9. The method of claim 1 wherein said dosage form comprises at least 20 wt. % of mannitol, lactose, sucrose, or a combination thereof.

10. The method of claim 1 wherein said dosage form comprises a surfactant.

11. The method of claim 1 wherein said dosage form comprises a surfactant having a hydrophilic lipophilic balance greater than 14.

12. The method of claim 1 wherein said dosage form comprises from about 30 to about 80 wt. % of a hygroscopic diluent and a freely soluble diluent at a weight ratio of from about 1:20 to about 5:1.

13. The method of claim 1 wherein said dosage form comprises an excipient base that is characterized by an inverse relationship between disintegration rate and moisture uptake.

14. The method of claim 1 wherein said excipient base comprises greater than about 20 wt. % of a freely and rapidly soluble diluent.

15. The method of claim 1 wherein said blister package is further imprinted with precautionary indicia discouraging the administration of the drug for the treatment of chronic pain.

16. The method of claim 15 wherein said precautionary indicia states that the safety of the drug has only been studied in short term studies or that the safety of the drug during long term administration has not been adequately investigated.

17. A method of treating acute pain in a host in need thereof comprising:
  a) providing diclofenac or a pharmaceutically acceptable salt thereof in a dosage form that comprises:
    i) an excipient base which has been demonstrated to yield a time to maximum plasma concentration ($t_{max}$) of from about 5 to about 40 minutes; and
    i) blister packaging divided into from five to fourteen medication segments, wherein each medication segment corresponds to one day of treatment, each medication segment is divided into from one to four unit doses corresponding to a daily dosage for said drug, and said blister packaging is imprinted with indicia that distinguishes between said medication segments and instructs on the proper treatment with said drug; and
  b) administering said diclofenac or pharmaceutically acceptable salt thereof to a patient suffering from acute pain
  wherein said dosage form comprises alkali metal carbonate or bicarbonate at a weight ratio to said diclofenac from about 1:5 to about 4:5.

18. The method of claim 17 wherein said blister packaging is further imprinted with precautionary indicia discouraging the administration of the drug for the treatment of chronic pain.

19. The method of claim 18 wherein said precautionary indicia states that the safety of the drug has only been studied in short term studies or that the safety of the drug during long term administration has not been adequately investigated.

20. A method of packaging an acute pain medication to discourage its administration in the treatment of chronic pain comprising:
  a) formulating said acute pain medication in a rapidly bioavailable dosage form which has been demonstrated to have a mean time to maximum plasma concentration ($t_{max}$) of from about 5 to about 40 minutes; and
  b) packaging said drug in a blister package divided into from five to fourteen medication segments, wherein:
    i) each medication segment corresponds to one day of treatment,
    ii) each medication segment is divided into from one to four unit doses corresponding to a daily dosage for said drug, and
    iii) said blister package is imprinted with indicia that distinguishes between said medication segments and instructs on the proper treatment with said drug;
  wherein diclofenac is the active ingredient of said medication; and
  wherein said dosage form comprises alkali metal carbonate or bicarbonate at a weight ratio to said diclofenac from about 1:5 to about 4:5.

21. The method of claim 20 wherein said blister package is further imprinted with precautionary indicia discouraging the administration of the drug for the treatment of chronic pain.

22. The method of claim 21 wherein said precautionary indicia states that the safety of the drug has only been studied in short term studies or that the safety of the drug during long term administration has not been adequately investigated.

* * * * *